(12) United States Patent
Nakamura

(10) Patent No.: US 8,679,050 B2
(45) Date of Patent: *Mar. 25, 2014

(54) GAS MIST PRESSURE BATHING COVER

(75) Inventor: Shoichi Nakamura, Higashichikuma-gun (JP)

(73) Assignees: ACP Japan Co., Ltd., Tokyo (JP); Shoichi Nakamura, Higashichikuma-gun, Nagano (JP)

(*) Notice: Subject to any disclaimer, the term of this patent is extended or adjusted under 35 U.S.C. 154(b) by 241 days.

This patent is subject to a terminal disclaimer.

(21) Appl. No.: 12/998,939

(22) PCT Filed: Mar. 9, 2010

(86) PCT No.: PCT/JP2010/053863
§ 371 (c)(1), (2), (4) Date: Jun. 17, 2011

(87) PCT Pub. No.: WO2010/104063
PCT Pub. Date: Sep. 16, 2010

(65) Prior Publication Data
US 2011/0257589 A1 Oct. 20, 2011

(30) Foreign Application Priority Data
Mar. 10, 2009 (JP) .................. 2009-055946

(51) Int. Cl.
*A61M 37/00* (2006.01)
(52) U.S. Cl.
USPC .................. 604/23; 601/151; 607/84
(58) Field of Classification Search
USPC ............. 604/23, 24; 607/83, 84, 91; 601/151, 601/152
See application file for complete search history.

(56) References Cited

U.S. PATENT DOCUMENTS 5,667,769 A * 9/1997 Kuckens et al. ............. 424/70.1
7,122,018 B2 * 10/2006 Stenzler et al. ................. 604/23

FOREIGN PATENT DOCUMENTS

| JP | 07-171189 | * 7/1995 |
| JP | 2004-113641 | 4/2004 |
| JP | 2005-058745 | 3/2005 |
| JP | 2007-260293 | 10/2007 |
| JP | U 3144717 | 8/2008 |

* cited by examiner

*Primary Examiner* — Theodore Stigell
*Assistant Examiner* — Deanna K Hall
(74) *Attorney, Agent, or Firm* — Manabu Kanesaka

(57) ABSTRACT

The present invention is to provide a gas mist pressure bathing cover which is simple in a structure and easy in pressurization. The gas mist pressure bathing cover 1, in which a mist (called as "gas mist" hereafter) is prepared at a density of not less than a predetermined value by pulverizing and dissolving carbon dioxide, oxygen, otherwise a mixed gas (called as "gas" hereafter) of carbon dioxide and oxygen and a liquid, and the thus prepared gas mist is contacted to the skin and mucous membrane of a living organism, comprises a living organism covering member 11 for covering the skin and mucous membrane of the living organism, a gas mist supply port 12 for introducing the gas mist into the living organism covering member and having a back-flow checking valve inside of the living organism covering member 11, a discharge port 13 for adjusting air, gas and pressure of the gas mist within the living organism covering member, and a pressure means 21 winding round an outer periphery of the living organism covering member at its opening portion in order to reduce its diameter and tighten the living organism covering member.

14 Claims, 8 Drawing Sheets

FIG.5
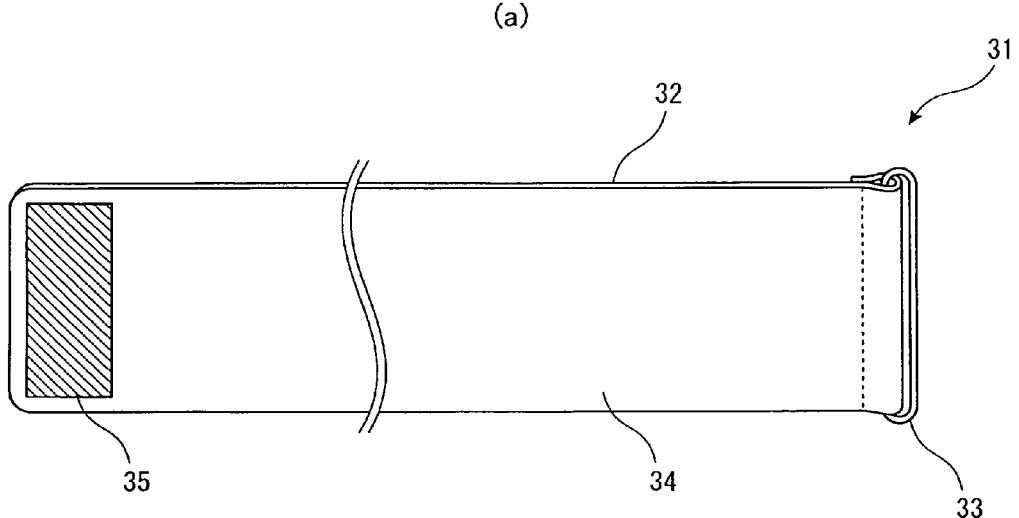
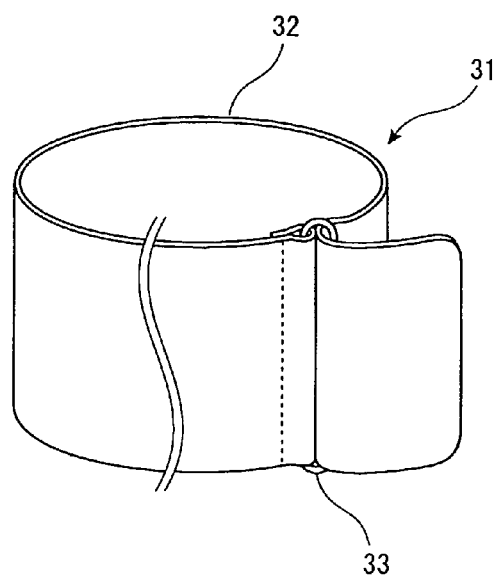 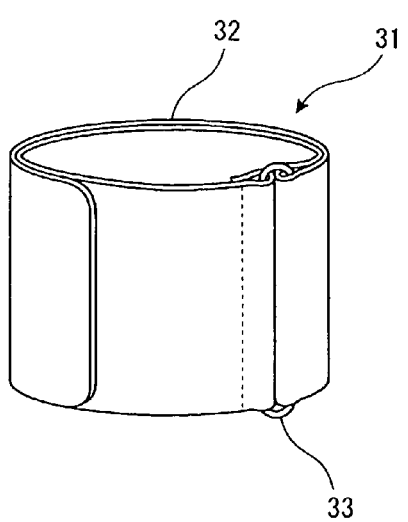

FIG.8
(a)
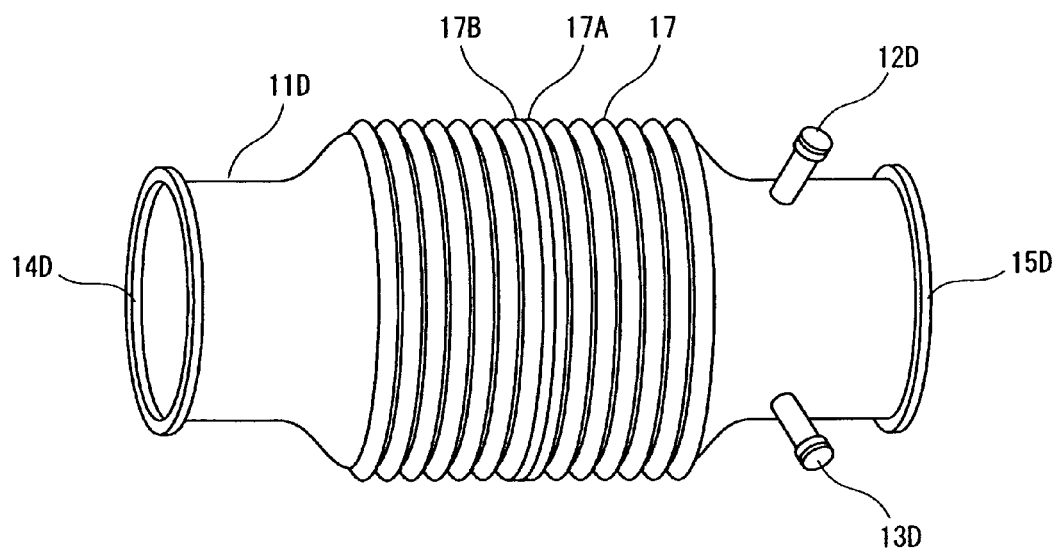
(b)
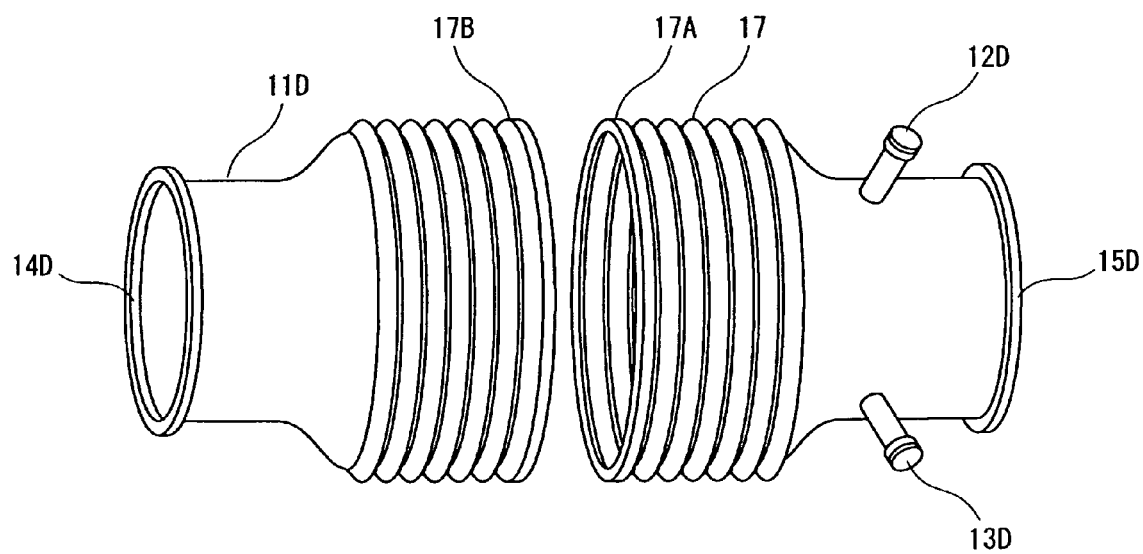

GAS MIST PRESSURE BATHING COVER

RELATED APPLICATIONS

The present application is National Phase of International Application No. PCT/JP2010/053863 filed Mar. 9, 2010, and claims priority from, Japanese Application No. 2009-055946 filed Mar. 10, 2009, the disclosure of which are hereby incorporated by reference herein in its entirety.

TECHNICAL FIELD

The present invention relates to a gas mist pressure bathing cover used to taking a gas mist pressure bath for directly contacting carbon dioxide, oxygen, otherwise a mixed gas of carbon dioxide and oxygen to a skin and a mucous membrane of a living organism.

BACKGROUND ART

It has conventionally been known that carbon dioxide (carbonic acid anhydride: $CO_2$) has both properties of being not only soluble in water (water-soluble) but also soluble in fat (fat-soluble) and, therefore, by only contacting the skin and mucous membrane of the living organism being like mixed with water and fat, carbon dioxide penetrates under a subcutaneous layer and expands blood vessels around the parts of penetrated carbon dioxide, and it works to improve the blood circulation. Owing to this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attentions also from viewpoints of improving health or beauty other than the purpose of medical cares.

Carbon dioxide in the tissue of the living organism works to release oxygen having been carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as having been combined with oxygen and the cell becomes unable to receive oxygen. As is seen, carbon dioxide seems to be a waste product resulted from action of the cell, however, it plays in fact very important roles in the living organism.

Further, in recent times, oxygen of the high density has also widely been known as effective in activity of metabolism, fatigue recovery, or stability of blood pressure.

Therefore, for directly absorbing carbon dioxide, oxygen, or the mixed gas of them into the skin and mucous membrane of the living organism, an inventor of this invention has proposed a gas mist pressure bathing device and a gas mist pressure bathing system, which seal the above mentioned gas into a gas mist pressure bathing cover of shielding the skin and mucous membrane and contact it to the skin and mucous membrane at predetermined pressure.

CITATION LIST

Patent Document

Patent Document 1: Japanese Patent Application Publication No. 2007-260293

SUMMARY OF INVENTION

Problems to be Solved by the Invention

However, a prior art gas mist pressure bathing cover used to gas mist pressure bathing has been difficult to carry out rapidly and effectively pressurization within the cover.

In view of the above circumstances, the present invention is to provide a gas mist pressure bathing cover which is simple in a structure and easy in pressurization.

Means for Solving the Problem

For solving the above mentioned problems, the present invention is to provide a gas mist pressure bathing cover, in which a mist (called as "gas mist" hereafter) is prepared at a density of not less than a predetermined value by pulverizing and dissolving carbon dioxide, oxygen, otherwise a mixed gas (called as "gas" hereafter) of carbon dioxide and oxygen and a liquid, and the thus prepared gas mist is contacted to the skin and mucous membrane of the living organism. The present invention is characterized by comprising a living organism covering member for covering the skin and mucous membrane of the living organism, a gas mist supply port for introducing the gas mist into the living organism covering member and having a back-flow checking valve inside of the living organism covering member, a discharge port for adjusting air, gas and pressure of the gas mist within the living organism covering member, and a pressure means winding round an outer periphery of the living organism covering member at its opening portion in order to reduce its diameter and tighten the living organism covering member.

By the way, the invention refers it as "pulverizing and dissolving" to pulverize the liquid into fine liquid drops, and cause to contact and mix with gas (carbon dioxide, oxygen, or the mixed gas of carbon dioxide and oxygen).

Preferably, at the opening portion of the living organism covering member, a stopper member is provided to avoid dropping of the pressure means.

The living organism covering member has desirably shapes of a bag, cylinder or pants.

In addition, at least one part of the living organism covering member is desirably shaped in cornice to be foldable. This cornice shape is divided at its one portion so that the living organism covering member is possible to open and close.

Herein, the above liquid is characterized to be any one or plural combination of water, ionic water, ozone water, physiological salt solution, purified water or sterilized and purified water.

In response to using purposes of the gas mist pressure bathing cover of this invention, the liquid may further contain any one or plural combination of menthol, vitamin E, vitamin C derivative, retinol, anesthetic, cyclodextrin, photo-catalyst, complex of photocatalyst and apatite, hyaluronic acid, coenzyme Q10, seed oil, propolis, ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate, high density carbonate spring, anti-allergic agent, anti-inflammatory agent, anti-febrile, anti-fungus agent, anti-influenza virus, influenza vaccine, steroid agent, carcino-static substance, anti-hypertensive agent, cosmetic agent, or trichogen.

Sizes of the gas mist introduced into the living organism covering member are suitably not more than 10 μm.

Advantageous Effects of Invention

According to the gas mist pressure bathing cover of the invention, it is possible to easily adjust pressure within the cover and effectively carry out the gas mist pressure bathing.

BRIEF DESCRIPTION OF DRAWINGS

FIG. 5 Typical views showing the outlines of the clamp for the gas mist pressure bathing cover depending on the second embodiment of the invention;

FIG. 8 Typical views (No. 2) showing the outlines of the living organism covering member of the folding system for the gas mist pressure bathing cover depending on the embodiments of the invention.

DESCRIPTION OF EMBODIMENTS

In the following description, explanations will be made to the embodiments of this invention, referring to the attached drawings.

First Embodiment

Figure 1:
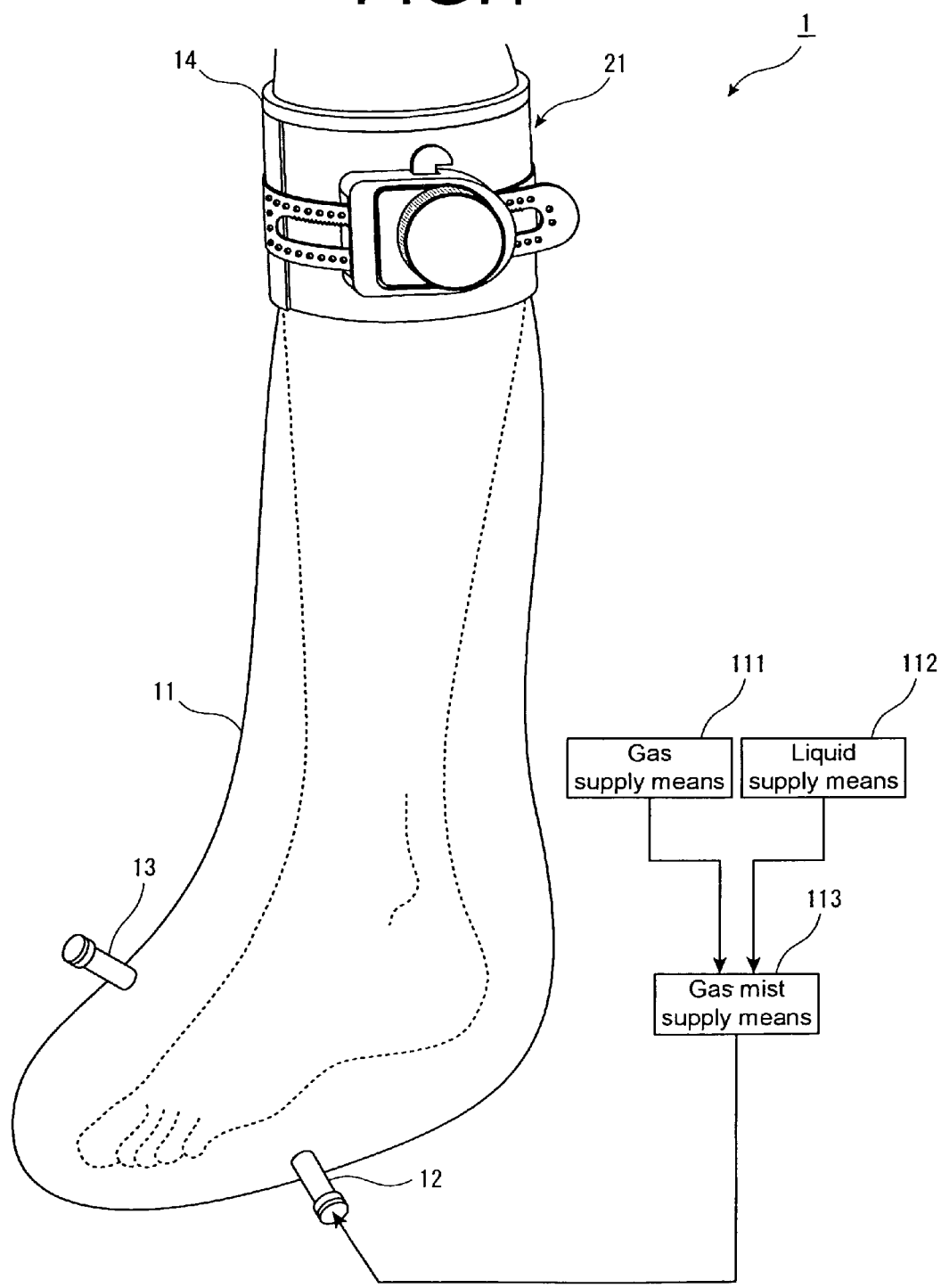
FIG. 1 A typical view showing the outline of the gas mist pressure bathing cover depending on the first embodiment of the invention.

Firstly, the gas mist pressure bathing cover of this embodiment will be explained together with the outlines of the gas mist pressure bath and the gas mist pressure bathing device applied with the gas mist pressure bathing cover of the invention. FIG. 1 is the typical view showing the outline of the gas mist pressure bathing cover depending on the first embodiment of the invention. The gas mist pressure bathing device is provided with a gas supply means 111 for supplying carbon dioxide, oxygen, otherwise carbon dioxide and oxygen (called briefly as "gas" hereafter), a liquid supply means 112 for supplying a liquid, a gas mist supply means 113 for changing the liquid from the liquid supply means 112 into fine liquid drops and generating to supply a mist (called as "gas mist" hereafter) prepared by pulverizing and dissolving the gas from the gas supply means 111, and the gas mist pressure bathing cover 1 formed with a space for sealing inside the supplied gas mist. A control device may be provided for supplying and controlling the gas, liquid and gas mist.

The gas supply means 111 supplies carbon dioxide, oxygen, otherwise carbon dioxide and oxygen into the gas mist supply means 113. For example, to use a gas bomb is optimum. Omitting illustration, the gas supply means 111 is desirably disposed with a regulator for adjusting pressure of the gas.

The liquid supply means 112 is composed of such as a pump and supplies the liquid to the gas mist supply means 113. As the liquid, it is suitable to use one or plural combination of water, ionic water, ozone water, physiological salt solution, purified water or sterilized water. Otherwise, it is good to use liquid medicines useful to user's diseases or symptoms.

Further, it is possible to generate synergistic effects with a gas physiological action by coupling these liquids with single or plurality of medicines as a menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the skin and mucous membrane; cyclodextrin removing a gas's odor; medicines sterilizing bacteria adhering to the skin and mucous membrane (for example, photocatalysis or a complex of photocatalysis and apatite); hyaluronic acid having excellent water holding capacity and a skin moisture retention effect; coenzyme Q10 activating cells and heightening immunization; a seed oil containing anti-oxidation and much nutrient; or propolis having anti-oxidation, anti-fungus, anti-inflammatory agent, pain-killing, anesthetic, and immunity. In addition, high density carbonate spring having main components of carbonate and organic acid (as examples of organic components, sulfate, carbonate or sodium dichloroisocyanurate) or sodium bicarbonate may be added. In the liquid supply means 112, it is desirable to dispose a heater (not shown) for heating the liquid (for example, heating to a hot water of around 40° C.) or a thermometer (not shown) for controlling temperature.

The gas mist supply means 113 generates the gas mist by changing the gas supplied from the gas supply means 111 and the liquid from the liquid supply means 112 into fine liquid drops, and supplies them into the gas mist pressure bathing cover 1. As to sizes of the mist generated at this time, being less than 10 μm is optimum. As the gas mist supply means 113, the mist generating devices of various systems may be employed, for example, a supersonic mist generating device, jet mist generating device, or fluid nozzle mist generating device.

Figure 2:
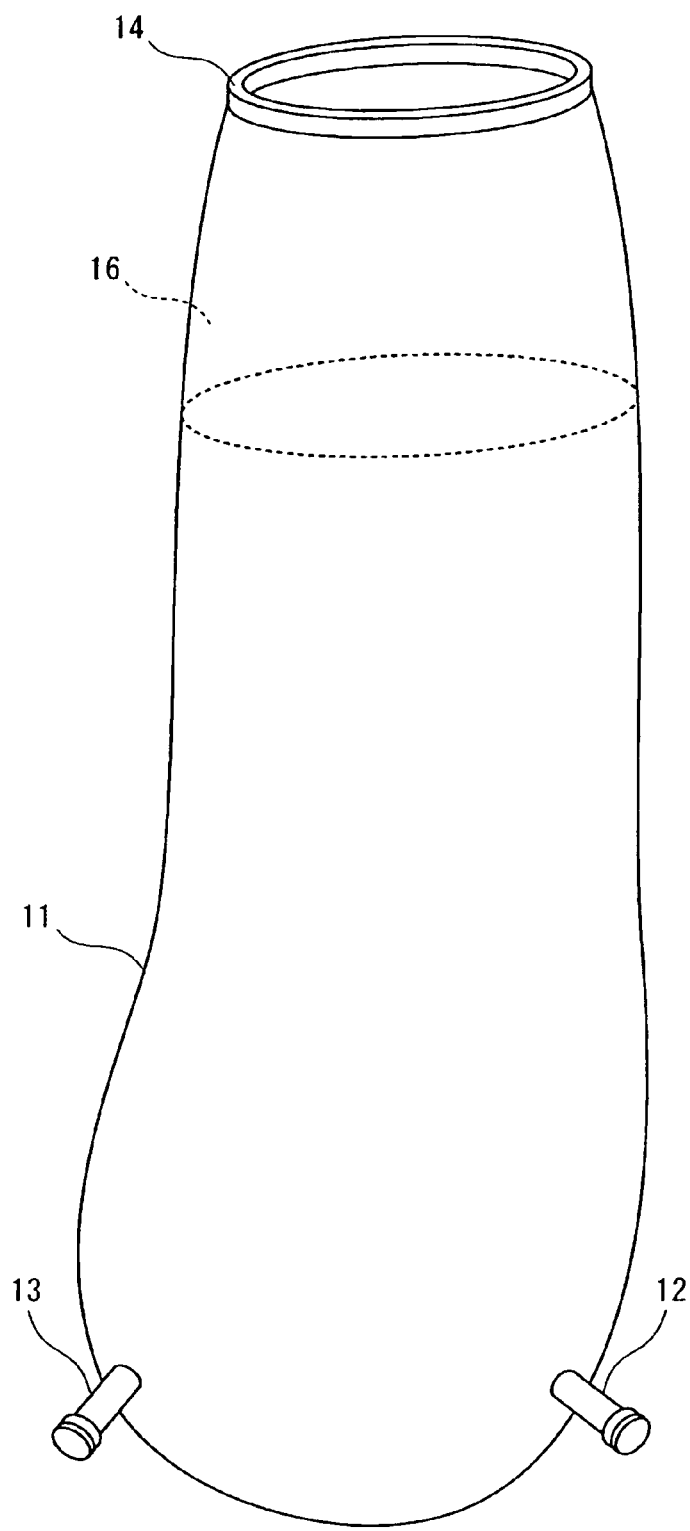
FIG. 2 A generally schematic view of the living organism covering member for the gas mist pressure bathing cover depending on the first embodiment of the invention.
Figure 3:
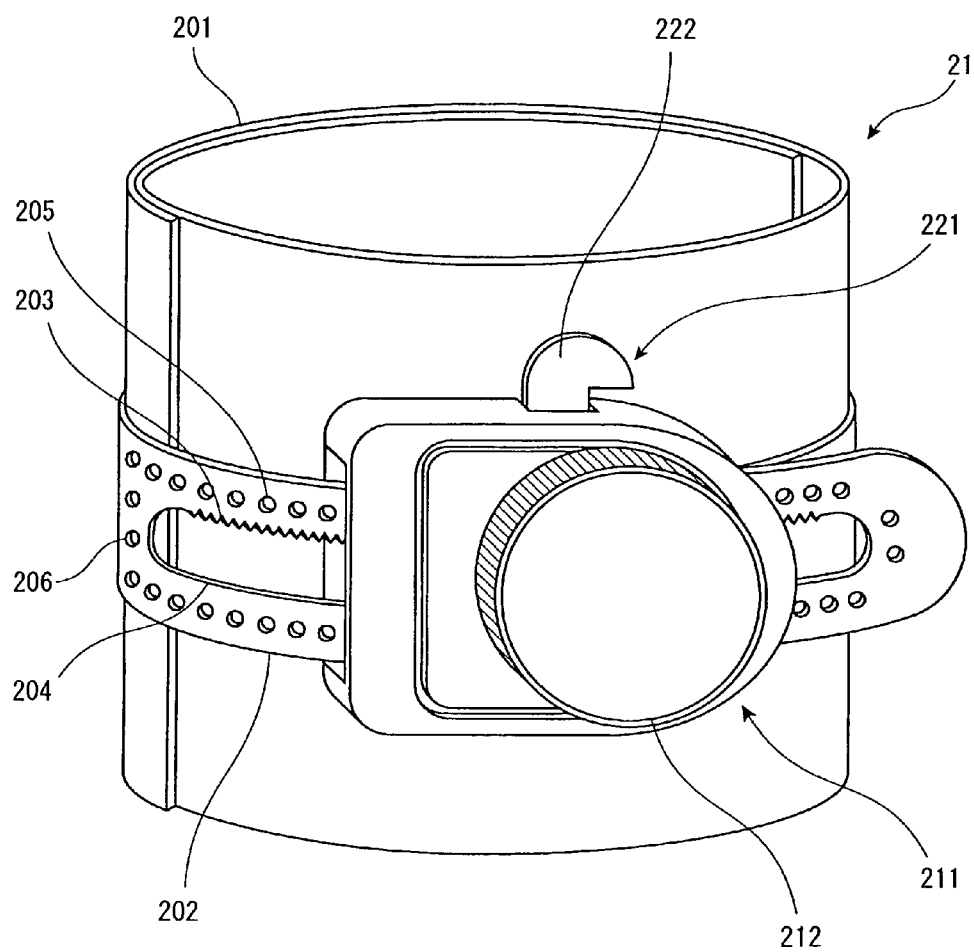
FIG. 3 A generally schematic view of the clamp for the gas mist pressure bathing cover depending on the first embodiment of the invention.

The gas mist pressure bathing cover 1 is a cover which covers the skin and mucous membrane of the living organism and can form a space of sealing the gas mist and gas inside thereof. As shown in FIG. 1, the gas mist pressure bathing cover 1 depending on the present embodiment is composed of the living organism covering member 11 having a shape (herein, a bag shape) of covering the skin and mucous membrane of the living organism as well as the clamp 21 serving as a pressure means attached to the outside of the living organism covering member 11 fastening moderately the living organism covering member 11 on its outer periphery. FIG. 2 shows an outline of the living organism covering member 11 and FIG. 3 is the outline of the clamp 21.

The living organism covering member 11 is, as shown in FIG. 2, furnished with a gas mist supply port 12 for introducing the gas and gas mist inside of this living organism covering member 11, a discharge port 13 for adjusting volume of pressure of air, gas or gas mist inside of the living organism covering member 11, and a stopper 14 provided at the opening portion of the living organism covering member 11 for avoiding slippage or displacement of the clamp 21 from the living organism covering member 11, and a cushion member 16 provided at the inside of the opening portion of the living organism covering member 11 for softening discomfort feeling caused by tightening.

The living organism covering member 11 is composed of a bag member having a size enabling to cover the part of the living organism as an object (herein, as the example, the lower extremity of the living organism), and is also composed of such non-permeable materials (preferably, polyvinyl chloride) having pressure resistibility against pressurization or flexibility having strength of more than a certain degree. Further, the living organism covering member 11 is desirable to be transparent or semitransparent, but since the visibility of the inside of the living organism covering member 11 is worsened by misting if filling the gas mist, it is good to treat a demisting coat on the inside.

The gas mist supply port 12 is an introducing part of the gas and gas mist communicating the inside of the living organism covering member 11. To this gas mist supply port 12, the gas mist supply means 113 and the gas supply means 111 are connected for supplying the gas and gas mist into the living organism covering member 11. For avoiding back flow of the gas and gas mist, it is desirable to dispose a backflow check valve within the gas mist supply port 12.

A discharge port 13 is an air hole for discharging air, gas and the gas mist from the living organism covering member 11 when discharging them from the same and adjusting pressure. The discharge port 13 has a structure which ordinarily prevents air blow by means of a valve or cap, and only when discharging as above mentioned, the valve is opened or the cap is unscrewed to enable air blow. This structure may open to discharge the gas and the gas mist when going beyond a predetermined pressure.

The stopper 14 is a thick and ring shaped member furnished following the opening of the living organism covering member 11 for preventing slippage or displacement from the opening when the clamp 21 is placed nearly the opening of the living organism covering member 11. For easily attaching the living organism covering member to, detaching from the living organism and defining no extra space when attaching, the stopper is suitably composed of an elastic member as a rubber.

The cushion member 16 is composed of a material having flexibility and elasticity such as urethane foam for releasing a clamped feeling by the clamp 21. For example, the inside of the cushion member 16 may be provide with a further material adhering to the skin and mucous membrane-within the living organism for increasing a sealing property of the living organism covering member 11. As the adherent material, a visco-elastic gel of, for example, polyurethane or silicone rubber is used. Preferably, the adherent material has a structure which can be detachably attached, and exchanged each time when using or viscosity becomes weak.

The present embodiment uses, as shown in FIG. 3, the clamp 21 having a clamping mechanism of rack and pinion. As an example, a clamping mechanism and a holding mechanism described in Japanese Patent Application Publication No. 2007-260293 (Patent Document 1) are employed.

This clamp 21 has a cushion belt 201, a tightening belt 202, a clamping mechanism 211 and a holding mechanism 221.

The cushion belt 201 is so provided as not to damage the living organism covering member 11 by contacting of the tightening belt 202, and this is made cylindrical of a long member which is overlapped at its end portions. The cylinder formed by the cushion belt 201 is variable in diameter according to actions of the clamping mechanism 211 and the holding mechanism 221.

The tightening belt 202 is a resin-made long member, and has a long opening portion 204 having a rack 203, upper and lower holding holes 205 of determined pitch following the opening portion 204, and through-holes 206 at parts not formed with the opening portion 204.

The clamping mechanism 211 has abase (not shown) fixed to the cushion belt 201, a knob 212 rotated by inserting of a rotating shaft (not shown) rotatably placed to the base, and a pinion gear (not shown) formed in the rear side of the knob 212 and in mesh with the rack 203 of the tightening belt 202. The tightening belt 202 is connected at its one end to the base and is inserted at the other end into a groove formed in the base. Further, under a condition where the pinion gear formed in the rear side of the knob 212 is inserted in the opening portion 204 of the tightening belt 202, the knob 212 fits the rotating shaft of the base. Thereby, if rotating the knob 212, the pinion gear also rotates, and by sending the rack 203, the tightening belt 202 and the cushion belt 201 reduce the diameters.

The holding mechanism 221 has a holding pin (not shown) inserting in the holding hole 205 of the tightening belt 202, a spring (not shown) biasing the holding pin toward the holding hole 205, and a releasing lever 222 for forcibly taking off the holding pin from the holding hole 205.

The holding pin is provided rotatably at the center of a shaft (not shown), and is free to get into or get out the holding hole 205. By the holding pin getting into the holding hole 205, the tightening belt 202 is restrained from moving to retain this position. Ordinarily, the holding pin is biased by a spring toward the holding hole 205, and if rotating the knob 212 to send the tightening belt 202 in the tightening direction, the holding pin is yielded by moving of the tightening belt 202 and goes off from the holding hole 205, and gets into a next holding hole 205 to hold the tightening belt 202. By repeating this action, the tightening belt 202 reduces the diameter to enable tightening.

When operating the releasing lever 222, the holding pin is forcibly rotated from the holding hole 205 in the releasing direction. Thereby, the holding pin separates from the holding hole 205, so that the tightening belt 202 expands the diameter and is released from tightening.

By the way, the structures of the tightening belt 202, the clamping mechanism 211 and the holding mechanism 221 of the above mentioned clamp 21 follow the description of Patent Document 1, and an only brief description is given here (as to the details, refer to Patent Document 1).

Accordingly, explanation will be made to the embodiment of the gas mist pressure bath using the clamp 21 having the above mentioned structure. Firstly, the living organism covering member 11 is attached to a part of the living organism, requesting a treatment of the gas mist pressure bath (herein, the lower extremity). At this time, air is discharged as much as possible from the opening portion or the discharging portion. Subsequently, the gas is supplied from the gas supply means 111, and the liquid is supplied from the liquid supply means 112 respectively into the gas mist supply means 113 for producing the gas mist. While closing the opening portion of the living organism covering member 11 with a hand, the gas mist from the gas mist supply means 113 is supplied to the living organism covering member 11 via the gas mist supply port 12. When the mist is enough supplied into the living organism covering member 11, only the gas is supplied from the gas supply means 111 into the living organism covering member 11. Then, in the living organism covering member 11, the gas is controlled to exist about 95 to 97%, while the liquid is controlled to exist about 3 to 5%. Next, the clamp 21 is positioned on the attached living organism covering member 11 nearly the opening as shown in FIG. 1, and the knob 212 is rotated to gradually reduce the diameters of the tightening belt 202 and the cushion belt 201. In this manner, the capacity of the living organism covering member 11 is narrowed and a moderately pressurizing condition can be provided. By the way, if requesting a fine adjustment when pressure is too high, or requesting or discharging the gas and the gas mist, air can be discharged from the discharge port 13. Depending on the above mentioned manner, the optimum gas mist pressure bathing is taken.

Second Embodiment

Figure 4:
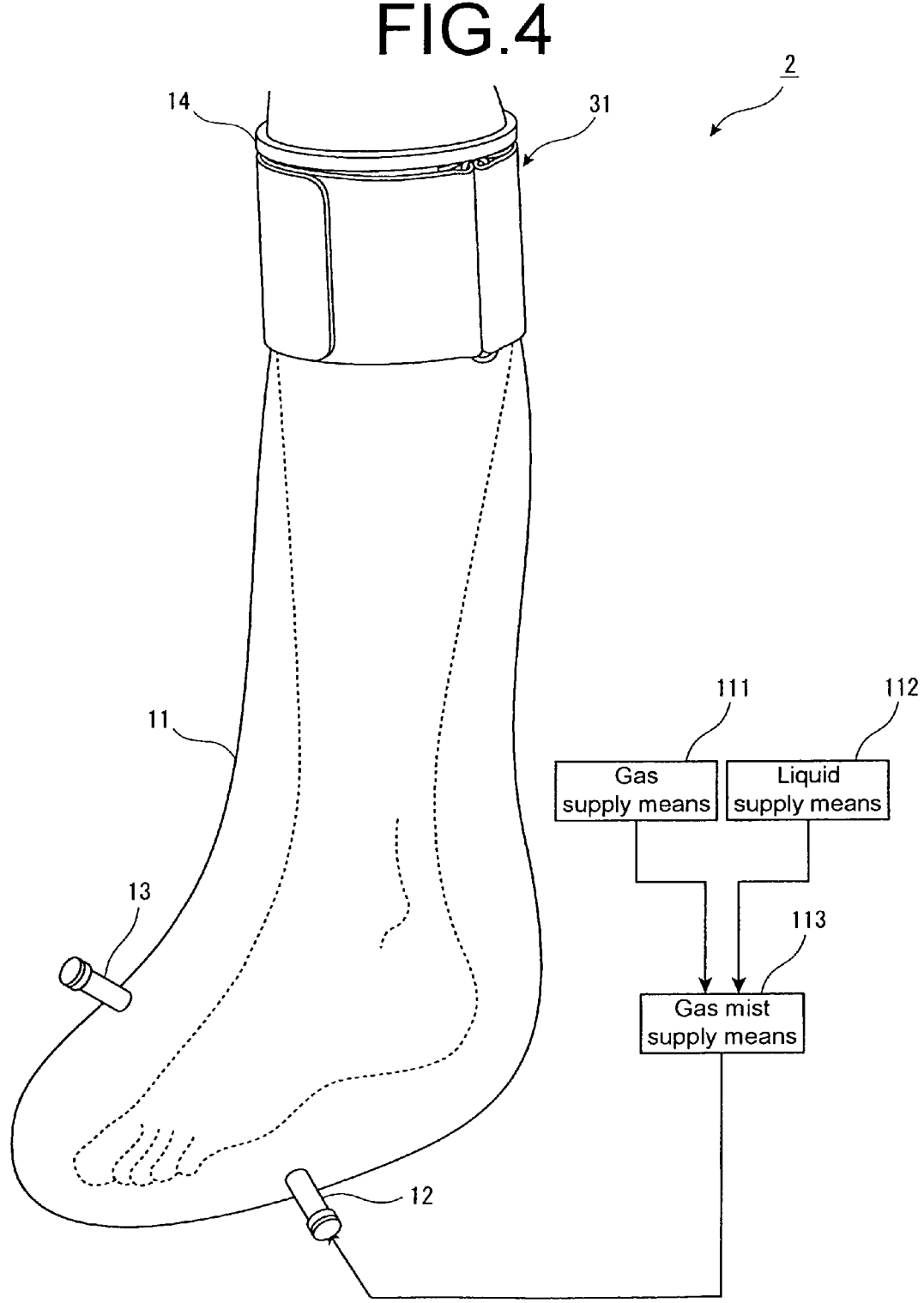
FIG. 4 A typical view showing the outline of the gas mist pressure bathing cover depending on the second embodiment of the invention.

FIG. 4 is the typical view showing the outline of the gas mist pressure bathing cover depending on the second embodiment of the invention. This embodiment shows an example of applying the clamp using a face fastener. As to the same parts as those of the first embodiment shown in FIG. 1, the same numerals will be given, and detailed explanation will be omitted.

As shown in FIG. 4, the gas mist pressure bathing cover 2 depending on the present embodiment is composed of the living organism covering member 11 having a shape (herein, a bag shape) for covering the skin and mucous membrane of the living organism as well as the clamp 31 serving as a pressure means attached to the outside of the living organism covering member 11 fastening moderately the living organism covering member 11 on its outer periphery. FIG. 5 shows the outline of the clamp 31.

The clamp 31 of this embodiment is, as shown in FIG. 5, composed of a tightening band 32 and a folding ring 33 furnished at one end of the tightening band 32.

The tightening band 32 is made of a soft and long member having elasticity and has the folding ring 33 at its one end. For furnishing the folding ring 33, for example, it is passed through the tightening band 32 at its one end, and the tightening band 32 is bent to hold the folding ring 33 at its end to make a ring-shape by stitching each other.

The tightening band 32 is formed on its surface with a loop portion 34 of the face fastener made of a fur napping and loop shaped fiber. In addition, the tightening band 32 is furnished with a hook portion 35 of the face fastener made of the fur napping and loop shaped fiber at the other end of not furnished with the folded ring 33.

For tightening, the clamp 31 is placed as shown in FIG. 4 nearly the opening of the attached living organism covering member 11, and as shown in FIG. 5(b), its end portion having the hook portion 35 is passed through the folding ring 33 from the inner side to the front side, and a ring shape is formed. If pulling the end portion having passed through the folding ring 33, the tightening band 32 shrinks at the diameter and moderately tightens the living organism covering member 11. As shown in FIG. 5(c), the tightening band 32 is returned from the folding ring 33 to secure the hook portion 35 at an arbitrary position by the loop portion 34. In this manner, the capacity of the living organism covering member 11 is narrowed and a moderately pressurizing condition can be provided.

Figure 6:
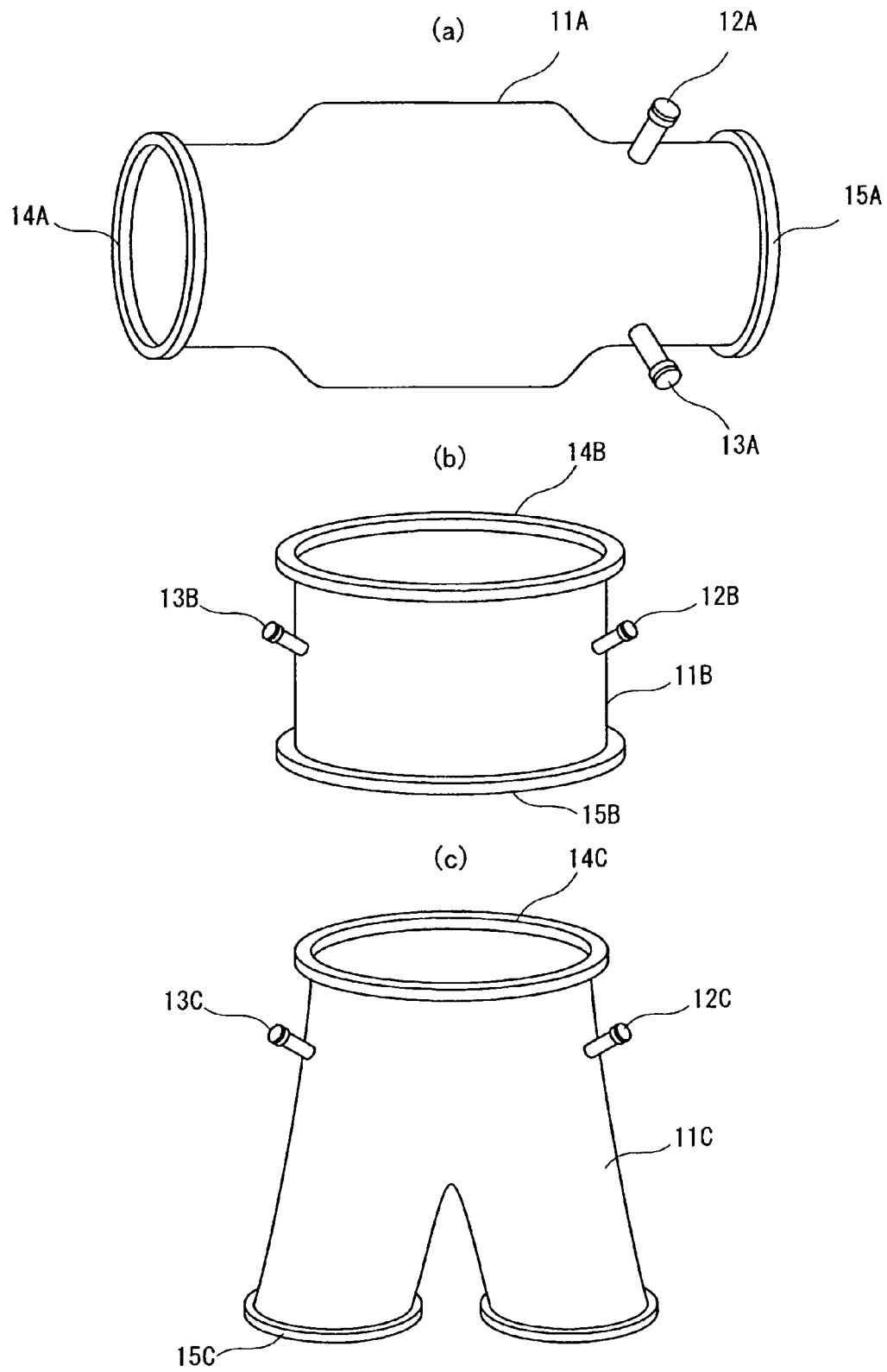
FIG. 6 Typical views of the living organism covering members having various configurations for the gas mist pressure bathing covers depending on the embodiments of the invention.

By the way, the above first and second embodiments have shown the examples of attaching the bag shaped living organism covering members 11 to the lower extremity (especially, below the knee) of the living organism, and of course, if changing the bag shapes, the living organism covering member 11 can be applied to the forearm, hand, foot or head. Following explanations will be made to living organism covering members being different in shapes. FIG. 6 is the typical views of the living organism covering members having various shapes.

FIG. 6(a) shows a cylindrical living organism covering member 11A. This is mainly suitable to attaching to long and narrow parts of the living organism. The cylindrical living organism covering member 11A has a gas mist supply port 12A and a discharge port 13A, and stoppers 14A, 15A at both ends. For taking the gas mist pressure bathing, the clamps are preferably arranged at both ends, but it is sufficient to arrange the clamp at one side only and close an opening portion at the other side with a string, rubber or face fastener.

FIG. 6(b) shows a cylindrical living organism covering member 11B of a large diameter. This is mainly suitable to performance of taking the gas mist pressure bathing from the chest to the abdomen or the neck. The living organism covering member 11B has a gas mist supply port 12B and a discharge port 13B, and stoppers 14B, 15B. For taking the gas mist pressure bathing, the clamps are preferably arranged at both ends, but it is sufficient to arrange the clamp at one side and only close an opening portion at the other side with a string, rubber or face fastener.

FIG. 6(c) shows a pants shaped living organism covering member 11C. This is suitable to performance of taking the gas mist pressure bathing from the lower abdomen to the inguinal region, buttocks to thigh. The living organism covering member 11C has a gas mist supply port 12C and a discharge port 13C, and has a stopper 14C at an opening of the upper portion (the side of the lower abdomen) and a stopper 15C at two openings of the lower portion (the side of the thigh). For taking the gas mist pressure bathing, the clamps are preferably arranged at both ends, but it is sufficient to arrange the clamp at one side and only close an opening portion at the other side with a string, rubber or face fastener.

Figure 7:
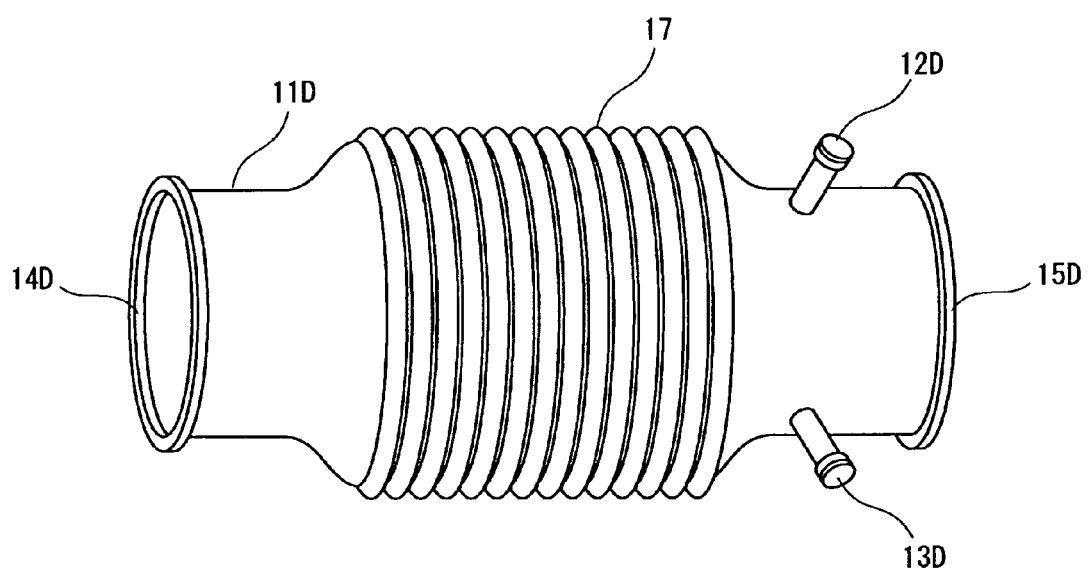
FIG. 7 A typical view (No. 1) showing the outline of the living organism covering member of the folding system for the gas mist pressure bathing cover depending on the embodiment of the invention.

Next, explanations will be made to living organism covering members of a folding system. FIGS. 7 and 8 are typical views showing the outlines of the living organism covering members of the folding system. As shown in FIG. 7, a living organism covering member 11D (herein, the cylindrical shape) has a cornice portion 17 at the center, and has a gas mist supply port 12D, discharge port 13D, and stoppers 14D, 15D at both ends. If having the cornice portion at one place as seen, the living organism covering member 11D can be folded to be small when not using. Further, as seen in FIG. 8(a), the living organism covering member 11D may be parted at one part of the cornice portion 17. To part is preferable at a portion almost central of the living organism covering member 11D. The parted portions 17A, 17B are, as shown in FIG. 8(b), possible to open and close as an accordion curtain, since connection and separation are arbitrary by a slip-in system. As is seen, since the living organism covering member 11D is possible to open and close at the cornice portion 17, another therapy may be combined, for example, the gas mist pressure bathing and an acupuncture are performed concurrently (after attaching the living organism covering member 11D to the living organism, the parted portions 17A, 17B are opened, and an acupuncture needle is applied, and after closing the parted portions 17A, 17B, the gas mist pressure bathing is carried out).

The above mentioned embodiments have shown the examples of applying the gas mist pressure bathing cover to the human living organism, but may be used to not only the human living organism but also animals.

With the structures as mentioned above, according to the gas mist pressure bathing cover of the invention, it is possible to easily adjust pressure within the cover and effectively take the gas mist pressure bathing.

The above explanation has been made to the embodiments of the invention, but the invention is not limited thereto, and so far as not deviating from the subject matter of the invention, various kinds of embodiments are, of course, available.

INDUSTRIAL APPLICABILITY

Thus, the present invention relates to the living organism covering member which directly contacts carbon dioxide, oxygen, otherwise the mixed gas of carbon dioxide and oxygen to the skin or mucous membrane of the living organism, with an Industrial applicability.

REFERENCE SIGNS LIST 1, 2: gas mist pressure bathing cover
11, 11A, 11B, 11C, 11D: living organism covering member
12, 12A, 12B, 12C, 12D: gas mist supply port
13, 13A, 13B, 13C, 13D: discharge port
14, 14A, 15A, 14B, 15B, 14C, 15C, 14D, 15D: stopper
16: cushion member
17: cornice portion
17A, 17B: parted portions
21, 31: clamp
32: tightening band
33: folding ring
34: loop portion
35: hook portion
111: gas supply means
112: liquid supply means
113: gas mist supply means
201: cushion belt
202: tightening belt
203: rack
204: opening portion
205: holding hole
206: through-hole
211: clamping mechanism
212: knob
221: holding mechanism
222: releasing lever

The invention claimed is:

1. A gas mist pressure bathing cover, adapted to prepare a gas mist at a density of not less than a predetermined value by pulverizing and dissolving carbon dioxide, oxygen, or a mixed gas of the carbon dioxide and the oxygen, and a liquid, and to contact the mist to a skin and mucous membrane of a living organism, comprising:
   a living organism covering member for covering the skin and mucous membrane of the living organism, and the living organism covering member including an opening portion;
   a gas mist supply port for introducing the gas mist into the living organism covering member, and the gas mist supply port having a back-flow checking valve inside the living organism covering member;
   a discharge port for adjusting air, the gas, and pressure of the gas mist within the living organism covering member;
   a pressure device winding round an outer periphery of the opening portion of the living organism covering member to reduce a diameter thereof and tighten the living organism covering member; and
   a stopper member disposed at the opening portion of the living organism covering member and preventing the pressure device from dropping or slipping when the pressure device winds round the outer periphery of the opening portion of the living organism covering member.

2. A gas mist pressure bathing cover according to claim 1, wherein the living organism covering member has a shape of a bag, a cylinder, or pants.

3. A gas mist pressure bathing cover according to claim 1, wherein the living organism covering member includes a cornice and is foldable.

4. A gas mist pressure bathing cover according to claim 3, wherein the cornice is divided at one portion so that the living organism covering member is capable of opening and closing at the one portion.

5. A gas mist pressure bathing cover according to claim 1, wherein the liquid is at least one selected from the group consisting of water, ionic water, ozone water, physiological salt solution, purified water, and, sterilized and purified water.

6. A gas mist pressure bathing cover according to claim 5, wherein the liquid further contains at least one selected from the group consisting of menthol, vitamin E, vitamin C derivative, retinol, anesthetic, cyclodextrin, photo-catalyst, complex of photocatalyst and apatite, hyaluronic acid, coenzyme Q10, seed oil, propolis, ethanol, gluconic acid chlorohexizine, amphoteric surface active agent, benzalkonium chloride, alkyldiamino ether glycin acetate, sodium hypo-chlorite, acetyl hydroperoxide, sodium sesquicarbonate, silica, povidone-iodine, sodium hydrogen carbonate, high density carbonate spring, anti-allergic agent, anti-inflammatory agent, anti-febrile, anti-fungus agent, anti-influenza virus, influenza vaccine, steroid agent, carcino-static substance, anti-hyper tensive agent, cosmetic agent, and trichogen.

7. A gas mist pressure bathing cover according to claim 1, wherein a particle size of the gas mist introduced into the living organism covering member is not greater than 10 μm.

8. A gas mist pressure bathing cover according to claim 1, wherein a shape of the stopper member is a ring shape, the stopper member is formed separately from the pressure device, and the stopper member is disposed at the opening portion of the living organism covering member when the pressure device winds round the outer periphery of the opening portion of the living organism covering member.

9. A gas mist pressure bathing cover according to claim 8, further comprising a cushion member having flexibility and elasticity, the cushion member is disposed inside the opening portion of the living organism covering member.

10. A gas mist pressure bathing cover according to claim 9, wherein the cushion member contains a material adhering to the skin and mucous membrane of the living organism.

11. A gas mist pressure bathing cover according to claim 10, wherein the material is a visco-elastic gel.

12. A gas mist pressure bathing cover according to claim 11, wherein the visco-elastic gel is made from polyurethane or silicone rubber.

13. A gas mist pressure bathing cover according to claim 1, wherein the living organism covering member is transparent or semitransparent, and the living organism covering member includes a demisting coat inside thereof.

14. A gas mist pressure bathing cover according to claim 1, wherein the pressure device is a face fastener including:
   a tightening band having a loop portion made of a fur napping and loop shaped fiber;
   a hook portion disposed on one end of the tightening band and made of a fur napping and loop shaped fiber to secure to the loop portion; and
   a folding ring disposed at another end of the tightening band, wherein the one end of the tightening band is passed through the folding ring, a diameter of the tightening band is reduced, and the tightening band is returned from the folding ring to secure the hook portion to the loop portion.

* * * * *